United States Patent [19]

Lawrence

[11] Patent Number: 4,859,613
[45] Date of Patent: Aug. 22, 1989

[54] IMMUNOASSAYS FOR GLUTATHIONE AND ANTIBODIES USEFUL THEREIN

[76] Inventor: David A. Lawrence, 38 Wellington Rd., Delmar, N.Y. 12054

[21] Appl. No.: 929,937

[22] Filed: Nov. 12, 1986

[51] Int. Cl.$^4$ ............................................. G01N 33/53
[52] U.S. Cl. ...................................... 436/548; 436/86; 435/7; 435/68; 435/172.2; 435/240.26; 435/240.27; 435/243; 435/948; 530/331; 530/345; 530/387; 530/806; 530/808; 530/809; 935/89
[58] Field of Search ............... 436/548, 86, 89; 435/7, 435/172.2, 243, 948, 68, 240.26, 240.27; 424/88, 93; 935/89; 530/387, 806, 808, 809, 331, 345

[56] References Cited

U.S. PATENT DOCUMENTS 4,639,420  1/1987  Schaffner ........................... 436/543

OTHER PUBLICATIONS

A. Meister and M. E. Anderson, "Glutathione", Ann. Rev. Biochem. 52: 711-60 (1983).
E. Hayes et al., Measuring Leukotrienes of Slow Reacting Substance of Anaphylaxis: Development of a Specific Radioimmunoassay, The Journal of Immunology, 131, 492-433 (1983).

Primary Examiner—Robert J. Warden
Assistant Examiner—Stephen C. Wieder
Attorney, Agent, or Firm—Pennie & Edmonds

[57] ABSTRACT

Monoclonal antibodies specifically immunologically reactive to thiol-modified glutathione and hybridoma cell lines producing such monoclonal antibodies. A method of producing antibodies specifically immunologically reactive with reduced glutathione by immunizing an animal using a thiol-modified glutathione, for example, a glutathione-N-ethylmaleimide-keyhole limpet hemocyanin conjugate. A method of utilizing the antibodies produced to quantitate the amount of reduced glutathione in a biological sample, to monitor glutathione-associated conditions, to monitor the formation of normal metabolic intermediates and to monitor the detoxification of foreign compounds.

27 Claims, 1 Drawing Sheet

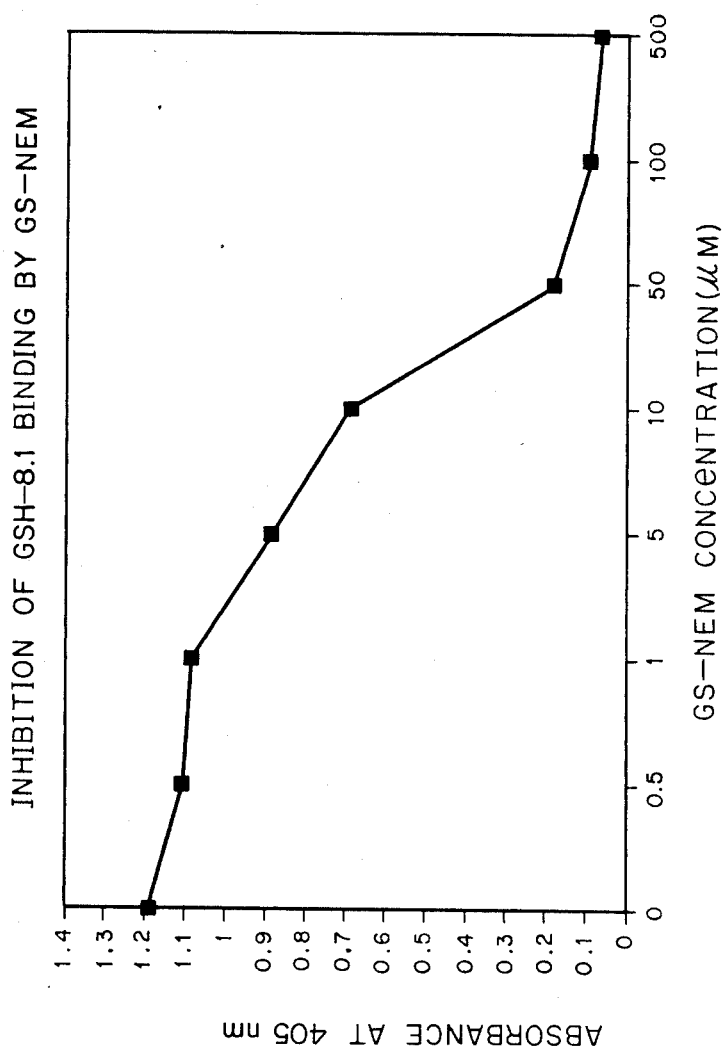

IMMUNOASSAYS FOR GLUTATHIONE AND ANTIBODIES USEFUL THEREIN

FIELD OF THE INVENTION

The present invention relates generally to antibodies which are specific to thiol-modified glutathione and which do not cross react with oxidized glutathione or naturally occurring conjugates of glutathione. More specifically, the invention relates to a method of raising monoclonal antibodies to thiol-modified glutathione. These monoclonal antibodies raised to thiol-modified glutathione can be utilized in immunoassays to quantitate the amount of reduced glutathione in a biological sample, to monitor glutathione-associated conditions, to monitor the detoxification of foreign compounds (such as some antineoplastic drugs), and to monitor the formation of normal metabolic intermediates such as estradiol-glutathione and prostaglandin-glutathione.

BACKGROUND OF THE INVENTION

The tripeptide glutathione (hereinafter abbreviated as GSH) is the most prevalent intracellular non-protein sulfhydryl found in biological systems [Meister and Anderson, Ann. Rev. Biochem. 52:711-60 (1983)]. The importance of GSH can be inferred from its many functions and its occurrence in a wide variety of organisms [Larson et al., Eds., *Functions of Glutathione*, Raven Press, New York (1983)]. Significant GSH levels have been detected in both unicellular and multicellular eukaryotes, as well as in plants and prokaryotic cells. In all of these different cell types, GSH functions either directly or indirectly in a number of enzymatic and metaboli processes. To date, known GSH functions include reductive processes essential for protein synthesis and degradation, formation of precursors necessary for DNA synthesis, various enzymatic and regulating activities, cellular transport systems, and protection of cells from oxidative stress generated by free radicals and reactive oxygen compounds. GSH is a coenzyme for several enzyme systems. GSH is also involved in the detoxification of a number of drugs, e.g., antineoplastic compounds and in the metabolism of some endogenous products, e.g., estrogens, leukotrienes, prostaglandins.

Recent studies have shown that GSH may have a prominent role in a number of other biological processes such as radiosensitivity, cancer therapy, oxygen toxicity, and modulation of immune responses. The study of GSH's functions extends to such diversified fields as toxicology, pharmacology, endocrinology, microbiology and agriculture [Meister and Anderson, Ann. Rev. Biochem. 52:711-60 (1983); Larson et al., Eds., *Functions of Glutathione*. Raven Press, New York (1983)].

GSH (L-$\gamma$-glutamyl-L-cysteinyglycine) is synthesized intracellularly in a series of enzymatic reactions of the $\gamma$-glutamyl cycle. In addition to the synthesis of GSH, the $\gamma$-glutamyl cycle is responsible for the extracellular transport of GSH and the GSH dependent transport of amino acids into the cell via $\gamma$-glutamyl transpeptidase. The combination of these reactions account for the cellular turnover of GSH [Meister, *Science* 220:472-77 (1983)].

GSH plays a major role in cellular oxidation-reduction reactions. The majority of intracellular GSH is found in the reduced state in cells under normal steady state conditions. Reduced GSH is reversibly oxidized either enzymatically by GSH-peroxidase or non-enzymatically to form the disulfide (hereinafter abbreviated as GSSG). A high ratio of GSH to GSSG is maintained in the cell; however, in cells undergoing oxidative stress, this ratio is altered. The high ratio is restored intracellularly by NADPH (nicotinamide adenine dinucleotide phosphate, reduced form) dependent GSSG reductase. There is no known extracellular mechanism for the reduction of GSSG; therefore, GSH must be supplied continuously by the cell to the extracellular environments [Giffith and Meister, Proc. Natl. Acad. Sci. (U.S.A.) 76:5606-10 (1979)]. The continuous transport of GSH into extracellular compartments suggests that it may have a role in the protection of cell membranes.

The sulfhydryl moiety of GSH assumes primary importance in protecting cells from oxidative insults. Cells are continuously exposed to a variety of endogenous and exogenous oxidants. Peroxides and free oxygen radicals are the most common since these are generated during normal metabolic processes as well as during exposure to ionizing radiation and/or increased oxygen tension. It is known that cellular GSH is the key to the oxygen effect in radiation damage [Biaglow et al., Radiat. Res. 95:437-55 (1983); Morse and Dahl, Nature 271:660-61 (1978); Stankova et al., J. Reticuloendothel. Soc. 21:97-102 (1977); Kowasaki, Intl. J. Radiat. Biol. 32:577-81 (1977)]. Oxidative stress is also imposed through the administration of drugs such as BCNU, adriamycin, and daunomycin and exposure to thiol alkylators such as organometals and alkyl halides [Arrick and Nathan, Cancer Res. 44:4224-32 (1984)]. Although other cellular mechanisms also exist for the removal of reactive oxygen intermediates, the participation of GSH, either directly or indirectly, in the oxidation-reduction cycle is of major importance in the maintenance of cellular function and structure.

GSH undergoes nucleophilic attack by a large variety of endogenous and exogenous compounds to form GSH conjugates. In this type of reaction, the reduced sulfhydryl group of GSH reacts with an electrophile to form a thioether. This reaction may occur spontaneously or may be catalyzed by GSH-S-transferases. GSH conjugates are readily transported across the cell membrane and converted to mercapturic acids in a series of reactions involving $\gamma$-glutamyl transpeptidase. Detoxification of foreign compounds (e.g., halogenated hydrocarbons, metabolites of ethanol and aromatic hydrocarbons) through this mechanism results in the formation of N-acetyl-S-substituted cysteines (mercapturic acids) which are ultimately excreted in the urine and feces.

Conjugates of GSH with endogenous compounds also occur under normal conditions and play an important role in the subsequent metabolism and activity of these compounds. For example, conversion to the $\Delta^5$-3-ketosteroids to the corresponding $\alpha$, $\beta$-unsaturated at $\Delta^4$-3-ketosteroids is catalyzed by liver proteins that appear to be identical with GSH-S-transferases [Meister and Anderson, ibid].

GSH also functions in several aspects of hormone, prostaglandin and leukotriene metabolism. For example, the reaction of the epoxide, leukotriene A, with GSH results in the formation of leukotriene C whose activity is different than the parent compound.

GSH may play numerous roles in cell transformation and tumor growth [Novi, Science 212:541-42 (1981); Zucker et al , FEBS Letters 155:107-11 (1983)]. Although ionizing radiation can inhibit proliferation of normal and neoplastic cells, low doses of ionizing radiation (<1000R) can produce the opposite effect, that is, induction of transformation. These inverse effects point out the need to better understand the mechanisms involved. Since antioxidants inhibit both effects, the ionizing radiation probably modulates thiol-dependent phenomena [(Arrick et al., J. Biol. Chem. 257:1231-37 (1984)]. The intracellular GSH levels are good correlates of radiosensitivity and may provide information on cell regulation of growth [Kennedy et al., Carcinogenesis 5:1213-18 (1984)]. Normal murine lymphocytes have 334±25 amole GSH/cell [Noelle and Lawrence, Biochem. J. 198:571 (1981)] and variants of a murine leukemic cell line (L5178Y) that are radioresistant (Do=84R) and radiosensitive (DO=35R) have 2540 and 870 amole GSH/cell, respectively [Alexander et al., In: Cellular Radiation Biology, Williams and Wilkins, Baltimore, p. 241, (1965)].

The involvement of cellular thiols in the regulatory mechanisms necessary for cell proliferation are well established. It has been suggested that thiol related reactions are involved in cancers; glyoxal derivatives (keto-aldehydes) inhibit cell proliferation and tumors lack keto-aldehydes [Szent-Gyorgyi, Science 155:539-41 (1967)]. Since keto-aldehydes are eliminated enzymatically by glyoxalases which utilize GSH, cellular thiols play a prominent role in regulating the concentration of these cancerostatic substances. Of course, the suggestion that glyoxal derivatives may be regulators of cell division and that regulation of their intracellular concentrations may be involved in cancer development is only one of many theories which have been suggested as an explanation for cancers. However, other theories also directly or indirectly have implicated cellular thiols in regulation or lack of regulation of cell growth [Lieberman and Gordon-Smith, Brit. J. Haemat. 44:425-30 (1980)]. Numerous studies have reported that blood GSH levels increase when animals or humans develop tumors, but the basis for this increase or the source of the GSH has not been delineated [Mills et al., J. Nutrition 3:1586-92 (1981)].

GSH may be involved in the development of autoimmune diseases. Numerous drugs used in the treatment of rheumatoid arthritis are thiol-reactive (e.g., d-penicillamine, levamisole, gold salts, and chloroquine) which suggest that thiols may be involved in the development or modulation of autoimmune diseases [Munthe et al., J. Rheumatol. (Suppl.) 7:14-19 (1978); Huck et al., J. Rheum. 11:605-09 (1984); Guber et al., Biochem. Pharm. 16:115-23 (1967)]. It has been reported that clinical improvement of rheumatoid arthritis by treatment with d-pencillamine can be predicted if there is an increase in intracellular GSH. Additionally, GSH levels are known to vary in patients with diabetes and some forms of diabetes are considered autoimmune diseases. GSH also is known to decrease with age and the incidence of autoimmunity increases with age.

DESCRIPTION OF THE PRIOR ART

Current methodologies employed to quantitate GSH suffer from a lack of specificity in that they measure either total non-protein thiols or total glutathione (GSH+GSSG), both of which are capable of erroneously inflating the true GSH value. Some of the present methods to quantitate GSH measure nonprotein thiols, usually consisting of 95% GSH. These assays and other biochemical assays for GSH [for examples, see Meister and Anderson, Ann. Rev. Biochem. 52:711-60 (1983)] are deficient in that:
1. they are non-specific for GSH;
2. they have low sensitivity;
3. they are time consuming;
4. they require protein precipitation;
5. they require the use of specialized and sophisticated equipment; and
6. they have relatively high costs.

None of the existing assays allow for the specific quantitative and/or qualitative analysis of GSH as associated on or within cells.

BRIEF DESCRIPTION OF THE DRAWINGS

FIG. 1 illustrates the concentration of thiol-modified glutathione required to inhibit a monoclonal antibody produced according to the invention.

SUMMARY OF THE INVENTION

The present invention provides a method for raising highly specific antibodies to thiol-modified GSH for use in assays which quantitatively and qualitatively assess reduced GSH or certain adducts intracellularly and extracellularly in biological samples. Highly specific antibodies to thiol-modified GSH are raised by first immunizing an animal with thiol-modified glutathione and then following standard methods to produce either polyclonal or monoclonal antibodies.

Any low molecular weight, thiol-reactive compound may successfully be used to modify the GSH molecule, as long as the antigenic determinant of GSH is not blocked. Since GSH is only a tripeptide (MW - 307.3 daltons), it is likely to have only one antigenic determinant.

DETAILED DESCRIPTION OF PREFERRED EMBODIMENTS

N-ethylmaleimide (hereinafter abbreviated as NEM) is a preferred thiol-reactive compound to conjugate to GSH (via the sulfhydryl group of GSH) in order to produce a thiol-modified glutathione complex for use as an antigen in accordance with the teachings of the present invention. NEM is preferred, because NEM has a highly specific reactivity with sulfhydryls, reacts in a rapid stoichiometric fashion, has a low molecular weight (125.1 daltons), is permeable to cells, and is readily accessible and inexpensive for most laboratories. In addition, the alkylation of GSH by NEM achieves two major purposes, namely:
 (1) the reaction slightly modifies the antigenic structure of GSH with modest stereochemical hindrance of the GSH structural portion; and
 (2) the reaction produces a purer, more uniform antigen (resulting in antibodies highly specific to reduced glutathione), because the rapid formation of conjugates (hereinafter referred to as GS-NEM) prevents the oxidation of GSH to GSSG or the random conjugation of GSH to other molecules.

Once the GS-NEM conjugate is formed, it would then be conjugated with a larger immunogenic carrier molecule such as keyhole limpet hemocyanin (hereinafter abbreviated as KLH). KLH is an excellent immunogen and can be used as a carrier molecule for haptens. As such, KLH stimulates a heightened immunological response to haptens which are conjugated to it.

The choice of crosslinking agents is extremely important since the structure of a crosslinking agent molecule and its length may influence the reactivity of the resulting antibody. A preferred crosslinking agent is therefore one with a simple repeating structure, which reacts with only one functional group from the carrier molecule and one functional group from the molecule to which it is to be conjugated. In addition, the length of the crosslinking agent is important because it determines the distance between the carrier and the hapten; it is desirable to keep the hapten just a short distance away from the carrier. The distance is extremely important inasmuch as it influences the binding site of the resulting antibodies.

Amino crosslinking agents are a preferred means of conjugating GS-NEM to an immunogenic molecule. Amino crosslinking agents, such as glutaraldehyde or bis(sulfosuccinimidyl) suberate, are ideal crosslinking agents for GS-NEM conjugation to a protein carrier; because only monomers of GS-NEM can be attached to the immunogenic carrier molecule due to the presence of only one reactive group for these crosslinking agents on GS-NEM [Sachs and Winn, Immunochemistry 7:581-85 (1970); Giedroc et al., J. Bio. Chem. 258: 16-19 (1983)]. Consequently, the antigenicity of GS-NEM will not be further altered except for the loss of hydrogen molecules from the amino groups as they are covalently linked to the carrier. The largest GS-NEM constituent not conjugated to the carrier protein will be dimers, which are easily removed by dialysis.

By employing conjugates of thiol-modified glutathione as immunogens, polyclonal and monoclonal antibodies can be raised using methods well-known in the art, such as those methods illustrated in the examples described below. Monoclonal antibodies are preferred because of their specificity. The antibodies thus raised are highly specific for a particular thiol-modified GSH complex.

The antibodies produced, preferably monoclonal antibodies, can then be used in immunoassays to quantitate the amount of thiol-modified or reduced glutathione present in a biological sample without first removing protein thiols. In contrast, glutathione assays in the prior art required the removal of protein thiols by protein precipitation before these assays could be carried out. The antibodies of this invention can be used in standard immunoassays such as radioimmunoassays, fluorescent immunoassays, or ELISA (enzyme linked immunosorbant assays). The amount of thiol-modified or reduced glutathione can be measured in biological materials like plasma, synovial fluids, aqueous humor, tissue homogenates, and cell lysates.

In addition, the monoclonal antibodies of the invention, can be conjugated to fluorescent dyes and used to assess the subcellular distribution of thiol-modified or reduced GSH by immunofluorescent microscopy and to quantitate the concentration per cell by flow microfluorescent cytometry.

In this manner, cells with variant GSH concentrations or distributions can be determined and biological samples with abnormal quantities of GSH can be evaluated for prognostic or diagnostic significance. Measuring the concentration of reduced GSH can be used to monitor the conditions where the ratio of reduced glutathione to oxidized glutathione (GSH/GSSG) is perturbed. As described above, such conditions include: oxidative stress due to drugs; ionizing radiation and increased oxygen tension; cancer; autoimmune diseases (including rheumatoid arthritis and diabetes); and aging.

The ability of GSH to react with a number of metabolic intermediates to form stable conjugates provides another important application for monoclonal antibodies to thiol modified GSH. Potent, biologically active compounds such as prostaglandins, estrogens and leukotrienes react with GSH either non-enzymatically or through enzymatically catalyzed reactions to form stable conjugates which may have new biological activities or which can be readily eliminated from the body [Jellinck and Elce, Steroids 13:711-18 (1969); Cagen et al., Biochim et Biophys. Acta 398:205-08 (1975)]. Thus, through this pathway the activites of these compounds which range from vasodepression to neurological and ultimately behavior modifications can be regulated [Cagen et al., J. Biol. Chem. 251:6550-54 (1976); Jellinck et al, Endocrinology 115:1850-56 (1984)]. Because many of the parent compounds are extremely unstable with a relatively short half-life it is important to monitor more stable intermediates as an indication of the levels of the parent compounds. The production of monoclonal antibodies to GSH conjugates of each of these compounds would provide a powerful tool for the measurement of these relatively stable intermediates.

The scope of the invention is further described in connection with the following examples which are set forth for the sole purpose of illustrating the preferred embodiments of the invention and which are not to be construed as limiting the scope of the invention in any manner.

EXAMPLES

A. Preparation of the Immunogen The immunogen, for the development of polyclonal and monoclonal antibodies reactive with GS-NEM, was GS-NEM conjugated to KLH via glutaraldehyde or bis(sulfosuccinimidyl) suberate. The GS-NEM-KLH complex is formed as follows:

(1) NEM conjugation to GSH to produce GS-NEM:

Five mmoles NEM (Sigma Chemical Co., St. Louis, Mo.) was solubilized in 5 ml phosphate-buffered saline (0.14 M NaCl, 0.01 M sodium phosphate buffer, pH 7.2; hereinafter abbreviated as PBS) plus 2.5 ml ethanol. To this solution, 1 mmole GSH (reduced form, free acid-crystalline, Sigma Chemical Co.) was added slowly while vortexing. The final solution was incubated 1 hour at 22° C., rotary evaporated at 45° C. to dryness, resuspended in 4.8 ml H$_2$O, aliquoted (0.5 ml) into tubes, lyophilized, and frozen at −70° C.

(2) GS-NEM conjugation to KLH to produce GS-NEM-KLH

A 0.5 ml aliquot of GS-NEM was brought to 22° C. and 25 microliters of GS-NEM were added to 5mg KLH in 1 ml PBS. The KLH (Calbiochem-Behring Corp., La Jolla, Calif.) was previously dialyzed against PBS to remove ammonium sulfate salts. To the GS-NEM and KLH mixture were added 12 microliters of 25% glutaraldehyde (Grade I, Sigma Chemical Co.). The reaction was allowed to proceed for 120 minutes at 4° C. Alternatively, 10 microliters of a 10 mM bis(sulfosuccinimidyl) suberate (Pierce Chemical Co., Rockford, Ill.) solution, in 0.05 M sodium phosphate, pH 7.4 can be added to the GS-NEM and KLH mixture. When bis(sulfosuccinimidyl) suberate is exployed to the amino crosslinking agent, the reaction is allowed to proceed for 30 minutes at 4° C. The reaction mixture (glutaraldehyde used as the crosslinking agent) was then dialyzed (3×1000-fold volume PBS). The final GS-NEM-KLH immunogen is aliquoted and stored at −70° C.

Monoclonal antibodies specific for other thiol-modified glutathiones, for example, estrogen-GS or prostaglandin-GS can be made in the identical manner to that described above except that NEM would be replaced with the specific endogenous compound such as estrogen [Jellinck, et al., Steroids 13:711–18 (1969) or prostaglandin $A_1$ [Cagen et al., J. Biol. Chem. 251:6550–54 (1976)] which are reactive with GSH. Following purification by HPLC these GSH-conjugates will be covalently linked to a larger immunogenic carrier molecule via amino crosslinking agent, as described previously, and used as immunogens.

B. Raising Rabbit and Mouse Antisera to the GS-NEM-KLH Immunogen

The immunogen (GS-NEM-KLH) was used to produce polyclonal rabbit and mouse antibodies to GS-NEM. For rabbit antisera, the immunogen was mixed with complete Freund's adjuvant (1:1, v/v) and the rabbits were injected intradermally with 1.0, 0.5, 0.5, and 0.5 mg of immunogen at 3, 2, 2, and 2 week intervals, respectively. The animals were bled one week after the final immunization.

The mice (BALB/c) were immunized in a similar fashion except the initial dose was 0.25 mg and all subsequent doses were 0.1 mg.

C. Testing the Reactivity of the Antisera to GS-NEM

The rabbit and mouse antisera were tested for reactivity to GS-NEM by standard solid phase radioimmunoassay or ELISA. [Yalow, 1980, Ann Rev. Biophys. Bioeng. 9:327–45; Voller et al, Manual of Clinical Immunology, Chapter 45, ASM Press, pp. 359-371 (1980)].

The antigen utilized for the development of these assays was GS-NEM coupled to bovine serum albumin (hereinafter abbreviated as BSA) via glutaraldehyde or bis(sulfosuccinimidyl) suberate; bis(sulfosuccinimidyl) suberate is the preferred crosslinking agent. The GS-NEM-BSA (crystalline BSA was obtained from Miles Scientific, Naperville, Ill.) complex was prepared utilizing the same conditions as described above for the preparation of the GS-NEM-KLH complex.

The first step to test the reactivity of the antisera to GS-NEM was to dissolve the GS-NEM-BSA complex in 0.5 M Carbonate buffer, pH 9.5 at a final concentration of 0.05 mg/ml or 0.10 mg/ml. Aliquots of this solution were added to individual wells of an Immunolon I microtiter plate (Dynatech Laboratories Inc., Alexandria, Va.). The plate was then incubated overnight at 4° C. Additional binding sites on the polystyrene well were blocked by the addition of 0.1 ml/well of a 0.02 m/ml solution of BSA in Carbonate buffer. Following a two hour incubation period at room temperature, the plate was washed three times with PBS containing 0.025% Tween 80 (hereinafter abbreviated as PBS-T). 0.10 ml of the appropriate dilution of antisera was added to each well, and the plate was incubated for four hours at room temperature. The contents of the wells were then removed, and the plate washed three times with PBS-T.

Next, the radioimmunoassay protocol for detection of bound antibodies consisted of the addition of rabbit antimouse immunoglobulin, radiolabeled with $^{125}$Iodine, to each well at a concentration of 100,000 counts/well. After an overnight incubation period at 4° C., the plate was washed four times to remove any unbound radioactivity. Bound radioactivity in individual wells was counted with a Searle Gamma counter.

Similarly, the ELISA protocol consisted of adding 0.10 ml of goat anti-mouse immunoglobulin conjugated to alkaline phosphatase to each well, followed by an incubation period of three hours at room temperature. The plate was then washed four times with PBS-T. Next, 0.10 ml of substrate for alkaline phosphatase (paranitrophenyl-phosphate at 1.0 mg/ml in diethanolamine buffer, pH 9.8) was added to each well. The plate was incubated for thirty minutes at 37° C., and the optical density of each well was determined at 405 nm, with a Bio-Tech Model EL310 plate reader.

D. Production of Hybridomas Producing Monclonal Antibodies Specific for Thiol-Modified Glutathione To produce the antibody-producing hybridomas, BALB/c female mice were immunized as described above, except that the last injection was 0.05 mg GS-NEM-KLH in PBS given intravenously. The spleen was aseptically removed three days later, a single-cell suspension produced and fused with a nonsecreting BALB/c plasmacytoma (P3X63Ag 8.653; ATCC CRL 1580) cell suspension using 50% polyethylene glycol-1000 solution (w/v). The fusion, outgrowth of the hybrids, and cloning of the hybridomas were carried out, pursuant to well-known procedures [Kennett et al., Eds., Monoclonal Antibodies, Plenum Press, N.Y. (1980); Kohler and Milstein, Nature 256:495–97 (1975)].

Specifically, the splenocytes and plasmacytoma cells were mixed in a 5:1 ratio. The cells were separated from the fusion mixture by centrifugation and gently resuspended in RPMI-1640 medium containing 20% fetal bovine serum (hereinafter abbreviated as FBS). The resuspended cell mixture was equally distributed among each of the 96 well of a sterile microtiter plate which contained $1 \times 10^5$ irradiated peritoneal cells (from BALB/C female mice) per well as feeder cells. All cultures were incubated at 37 C under an atmosphere of 8% $CO_2$. The following day, approximately 0.10 ml of the culture media was aspirated from each well and replaced with media selective for hybrids. The medium used consists of RPMI-1640 with 20% FBS, plus hypoxanthine (0.1mM), aminopterin (0.8μM), and thymidine (16μM) (this medium is hereinafter abbreviated as HAT). The cells were fed every other day with HAT medium, following the procedure outlined above. Outgrowth of hybrids was visually detected and the culture supernatant from presumptive hybrid-containing wells was tested for the production of antibodies to GS-NEM by the ELISA assay described above. The products of some cloned hybridomas have been characterized, as discussed below.

E. Maintenance of Hybridoma Cell Lines and Antibodies

The maintenance of all hybridoma cells consisted of serial passage in RPMI-1640 with 20% FBS. Supernatants containing the secreted antibody was obtained by centrifugation of the cultures at 1000 RPM for 10 minutes to sediment out the cells. The supernatant was stored at −20° C. until use.

Ascites fluid containing monoclonal antibodies was produced by injecting $5 \times 10^6$ hybridoma cells into the peritoneal cavity of Balb/c mice which had been previously injected intraperitoneally with 0.5 ml of Pristane and given 250R 6 hours prior to injection of hybridoma. Mice were then monitored. When abdominal distention due to the growth of the tumor became pronounced, the fluid was aspirated from the peritoneal cavity into a syringe. The fluid was transferred into sterile centrifuge tubes and the cells sedimented by centrifugation. The cell-free ascites fluid was stored at −20° C. until use.

Antibodies were concentrated from either the ascites fluid or culture supernatants by precipitation with 50% ammonium sulfate. The ammonium sulfate was removed by dialysis against PBS and the antibodies concentrated and stored at −20° C.

F. Analysis of Antisera and Monoclonal Antibodies to GS-NEM

Two clones of hybridomas, producing monoclonal antibodies specific for thiol-modified glutathione, have been characterized and designated 8.1-F8-G1 and 8.1-D10-E8 (8.1 GSH). Hybridoma 8.1-D10-E8 (8.1 GSH) was deposited with the American Type Culture Collection, located at 12301 Parklawn Drive, Rockville, Md. and assigned Accession No. HB 9074. The produced and secreted by the clones designated 8.1-F8-G1 and 8.1-D10-E8 (8.1 GSH) are respectively IgM and IgG1.

The antibody reactivities of these immunoglobulins and those of the polyclonal rabbit and mouse antisera are shown in Tables 1 and 2. The IgG1 monoclonal antibodies produced by hybridoma clone 8.1-D10-E8 (8.1 GSH) are highly specific for GS-NEM. Table 3 shows the titer of the supernatant from cultured 8.1-D-10-E8 (8.1 GSH) cells, and the titer of the ascitic fluid produced when 8.1-D10-E8 (8.1 GSH) cells were passaged in Pristane-primed BALB/c mice. The assays were as described previously in Section VII. C., and used glutaraldehyde as the crosslinking agent, whenever required.

TABLE 1

Analysis of Antisera and Monoclonal Antibodies to GS-NEM[a]

| Antibodies | Inhibitor | CPM/Well | % Inhibition |
|---|---|---|---|
| Rabbit Antiserum (9/3/83) | None | 46,074 | 0 |
| | GS-NEM $10^{-5}$ M | 13,427 | 71 |
| | GS-NEM $10^{-6}$ M | 15,282 | 66 |
| | GS-NEM $10^{-7}$ M | 27,754 | 40 |
| | CYS-NEM $10^{-5}$ M | 25,945 | 44 |
| | CYS-NEM $10^{-6}$ M | 37,235 | 19 |
| | CYS-NEM $10^{-7}$ M | 42,937 | 7 |
| Mouse Antiserum (6/5/84) | None | 8,487 | 0 |
| | GS-NEM $10^{-3}$ M | 3,916 | 54 |
| | CYS-NEM $10^{-3}$ M | 8,901 | 0 |
| 8.1-D10-E8 (8.1 GSH) (IgG1) (12/27/84) | None | 20,226 | 0 |
| | GS-NEM $10^{-3}$ M | 1,893 | 91 |
| | CYS-NEM $10^{-3}$ M | 19,935 | 5 |

[a]Analysis was by inhibition solid phase radioimmunoassay. Background binding without antisera or antigen was 50–149 cpm/well.

TABLE 2

Analysis of IgG1 and IgM Monoclonal Antibodies[b]

| Antibodies | Inhibitor | OD405/well | CPM/well | % Inhibition |
|---|---|---|---|---|
| 8.1-D10-E8 (8.1 GSH) (IgG1) Ascites, (11/11/84) | — | 0.827 | ND | 0 |
| | GS-NEM $10^{-7}$ M | 0.608 | ND | 27 |
| | CYS-NEM $10^{-7}$ M | 0.810 | ND | 2 |
| 8.1-F8-G1 (IgM) Ascites (11/1/84) | — | ND | 9647 | 0 |
| | GS-NEM $10^{-4}$ M | ND | 7444 | 22 |
| | CYS-NEM $10^{-4}$ M | ND | 8249 | 15 |

[b]Analysis was by inhibition solid phase radioimmunoassay (cpm/well) or ELISA with alkaline phosphatase (OD405/well).

TABLE 3

ELISA TITRATION OF SUPERNATANT FLUIDS FROM HYBRIDOMA 8.1-D10-E8 (8.1 GSH)(IgG1)

| RECIPROCAL DILUTION | CULTURE SUPERNATANT (3/17/85) OD at 405 nm | ASCITES (12/27/84) OD at 405 nm |
|---|---|---|
| Control (Background) | .060 | .026 |
| 16 | .347 | ND |
| 32 | .369 | ND |
| 64 | .284 | ND |
| 128 | .296 | ND |
| 256 | .273 | ND |
| 512 | .175 | .885 |
| 1,000 | .168 | .839 |
| 2,500 | .125 | ND |
| 5,500 | .097 | 1.065 |
| 10,000 | .093 | .934 |
| 25,000 | ND | .834 |
| 75,000 | ND | .613 |
| 100,000 | ND | .538 |
| 250,000 | ND | .331 |
| 500,000 | ND | .173 |
| 750,000 | ND | .148 |
| 1,000,000 | ND | .152 |

The reactivity of monoclonal antibody from hybridoma clone 8 1-D10-E8 (8.1 GSH) is also demonstrated in FIG. 1; FIG. 1 is a graph showing the concentration of GS-NEM required to inhibit the monoclonal antibody from binding in an ELISA assay. Specifically, aliquots of monoclonal antibody 8.1-D10-E8 (8.1 GSH) at a dilution of 1:10,000 were incubated with serial dilutions of GS-NEM (0.5–500 μM) for 30 minutes at 37? C. The incubated mixtures were then added to the wells of microliter plate previously coated with BSA-GS-NEM. The BSA was conjugated to GS-NEM via bis(sulfosuccinimidyl) suberate. The plates were developed by the addition of goat anti-mouse IgG conjugated to alkaline phosphatase, followed by a substrate for alkaline phosphatase such as paranitrophenyl-phosphate. The details of performing the assay are the same as previously described in Section VII. C.

G. Testing Clinical Specimens Using Antibodies Specific to Thiol-Modified Glutathione

1. Heterogeneous Assays

Antibodies specific to thiol-modified GSH can be used to measure GSH in clinical specimens, using the previously described ELISA assays. One such assay consists of coating the wells of a microtiter plate (the solid phase) with a protein carrier bound to GS-NEM, preferably via bis(sulfosuccinimidyl) suberate. Any additional reactive sites on the solid phase are blocked by adding BSA and then incubating the plate for 60 minutes at room temperature. Any unbound antigen or blocker is removed by washing the wells with a constant stream of PBS-T. These plates can then be stored at −20° C. for later processing or can be utilized immediately by the addition of an appropriate dilution of the anti-GS-NEM antibody which has been exposed to various concentrations of free GS-NEM.

The free GS-NEM competes with the immobilized GS-NEM for binding sites on the anti-GS-NEM antibody molecules, thus, the amount of antibody bound to the solid phase is inversely proportional to the amount of free GS-NEM added. The amount of bound antibody can be visualized, as described previously, by the sequential addition of an enzyme-labeled anti-species antibody and substrate. In this fashion, a linear standard curve for known concentrations of inhibitor can be obtained Patient samples to be tested for their GSH content, such as serum, urine and other body fluids or detergent (NP-40) cell lysates, are pretreated with an excess of NEM for 30 minutes; then, aliquots of the same sample are tested for their ability to inhibit anti-GS-NEM antibody binding to the solid phase. The inhibition observed can then be used to extrapolate the concentration of GS-NEM in the sample from the standard curve. The concentration of reduced GSH in the sample is thus measured; since only the reduced form of GSH binds to NEM to form adducts and the anti-GS-NEM antibody is specific for these adducts.

An alternative, more direct, inhibitory assay consists of immobilizing purified monoclonal antibody to GS-NEM on the solid phase affinity plate. As in the previous assay, excess binding sites would be blocked by the addition of BSA and non-bound reagents removed by washing with PBS-T. At this point, the plates can be stored at -20° C or used immediately. A constant amount of labeled (biotin, fluorescent compound, radio-isotope, etc.) GS-NEM mixed with known concentrations of unlabeled GS-NEM is added to each well of anti-GS-NEM-monoclonal antibody coated plates. Since binding of labeled GS-NEM is inversely proportional to the concentration of unlabeled GS-NEM, a standard curve is generated.

As in the previous assay, a patient sample is treated with NEM and mixed with the labeled GS-NEM. The amount of inhibition then observed can then be extrapolated to calculate the amount of reduced GSH concentration present, using the standard curve as described above.

2. Homogeneous Assays

The assays described above are heterogeneous immunoassays in that they require a solid phase to immobilize the complexes formed by the reactive species. Another type of immunoassay is the homogeneous assay, which dispenses with the solid phase.

In a homogeneous assay system, the GS-NEM is enzyme-labeled. When antibody against GS-NEM is bound to the enzyme-labeled GS-NEM substrate, the activity of the enzyme is reduced. The GS-NEM adducts formed in a patient sample (following treatment with NEM) would then compete with the enzyme-labeled GS-NEM for the antibody, thereby decreasing the antibody-induced inactivation of the enzyme. The residual enzymatic activity is directly proportional to the concentration of the GSH present in the sample and is measured by a change in absorbance, resulting from the enzyme's catalytic action on the substrate.

Using such assays, linear standard curves are constructed, utilizing GS-NEM concentrations in the range of $1 \times 10^{-4}$ to $1 \times 10^{-7}$ M These curves indicate that the assays are sufficiently sensitive to detect physiological as well as non-physiological concentrations of GSH in patient samples.

H. Testing Intracellular GSH Pools

Antibodies to thiol-modified GSH can also be used as reagents to monitor alterations in intracellular GSH pools before, during and after exposure of the cells to various experimental conditions, such as radiation or toxic drugs. In an assay of this type, cells are treated with NEM and fixed with various fixatives capable of preserving the intracellular architecture while rendering the plasma membrane permeable to antibody molecules. These fixed cells are then incubated with anti-GS-NEM antibody for a short period of time (approximately 30 minutes at 4° C.) and excess antibody removed by washing. Next, a fluorescent-labeled anti-mouse antibody is added. After removal of excess unbound reagent, the cells are analyzed by fluorescent microscopy and by flow cytometry to determine the localization of the antibody in various cell types, under different conditions and at different times in the cell cycle.

Similarly, antibodies specific to estrogen-GS, prostaglandin-GS or leukotriene-C can be used in assays as illustrated above.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. An immunoassay for measuring the amount of reduced glutathione in a biological sample comprising the steps of:
   (a) contacting reduced glutathione that has been converted to a thiol-modified glutathione in said biological sample with at least one antibody specific for said thiol-modified glutathione to form a complex with said antibody and said thiol-modified glutathione, and
   (b) measuring the amount of reduced glutathione in said biological sample by means of said complex.

2. The immunoassay of claim 1 wherein said antibody is a monoclonal antibody.

3. The immunoassay of claim 1 wherein said thiol-modified glutathione is GS-NEM.

4. The immunoassay of claim 3 wherein said antibody is a monoclonal antibody specifically reactive with GS-NEM.

5. The immunoassay of claim 4 wherein said monoclonal antibody is produced by the hybridoma cell line A.T.C.C. HB 9074.

6. The immunoassay of claim 1 wherein said immunoassay is utilized to monitor a glutathione-associated condition.

7. The immunoassay of claim 6 wherein said glutathione-associated condition is selected from the group consisting of cancer, autoimmune diseases, oxidative stress, and ionizing radiation damage.

8. The immunoassay of claim 1 wherein said immunoassay is utilized to monitor the detoxification of foreign compounds.

9. The immunoassay of claim 8 wherein said foreign compound is selected from the group consisting of halogenated hydrocarbons, metabolites of ethanols and metabolites of aromatic hydrocarbons.

10. An immunoassay for measuring the amount of oxidized glutathione in a biological sample comprising the steps of:
    (a) contacting oxidized glutathione in said biological sample with at least one antibody specific for said oxidized glutathione to form a complex with said antibody and said oxidized glutathione, and
    (b) measuring the amount of oxidized glutathione in said biological sample by measuring the amount of said complex.

11. The immunoassay of claim 10 wherein said antibody is a monoclonal antibody.

12. An immunoassay for measuring the amount of estrogen-GS in a biological sample comprising the steps of:
   (a) contacting estrogen-GS in said biological sample with at least one antibody specific for said estrogen-GS to form a complex with said antibody and said estrogen-GS, and
   (b) measuring the amount of estrogen-GS in said biological sample by measuring the amount of said complex.

13. The immunoassay of claim 12 wherein said antibody is a monoclonal antibody.

14. The immunoassay of claim 12 wherein said immunoassay is utilized to monitor the metabolite intermediate estrogen.

15. An immunoassay for measuring the amount of prostaglandin-GS in a biological sample comprising the steps of:
   (a) contacting prostaglandin-GS in said biological sample with at least one antibody specific for said prostaglandin-GS to form a complex with said antibody and said prostaglandin-GS, and
   (b) measuring the amount of prostaglandin-GS in said biological sample by measuring the amount of said complex.

16. The immunoassay of claim 15 wherein said antibody is a monoclonal antibody.

17. The immunoassay of claim 15 wherein said immunoassay is utilized to monitor the metabolite intermediate prostaglandin.

18. A monoclonal antibody specifically reactive with GS-NEM.

19. The monoclonal antibody according to claim 8 wherein the monoclonal antibody is produced by the hybridoma cell line A.T.C.C. HB 9074.

20. A hybridoma cell line producing a monoclonal antibody specific for GS-NEM.

21. The hybridoma cell line according to claim 20 wherein said hybridoma cell line is A.T.C.C. HB 9074.

22. A monoclonal antibody specifically reactive with estrogen-GS.

23. A hybridoma cell line producing a monoclonal antibody specifically reactive with estrogen-GS.

24. A monoclonal antibody specifically reactive with prostaglandin-GS.

25. A hybridoma cell line producing a monoclonal antibody specifically reactive with prostaglandin-GS.

26. A monoclonal antibody specifically reactive with oxidized glutathione.

27. A hybridoma cell line producing a monoclonal antibody specifically reactive with oxidized glutathione.

* * * * *